US005635180A

United States Patent [19]

Morgan, Jr. et al.

[11] Patent Number: 5,635,180
[45] Date of Patent: Jun. 3, 1997

[54] ALTERATION OF PHARMACOKINETICS OF PROTEINS BY CHARGE MODIFICATION

[75] Inventors: Alton C. Morgan, Jr.; Gowsala P. Sivam, both of Edmonds; Paul G. Abrams, Seattle, all of Wash.

[73] Assignee: NeoRx Corporation, Seattle, Wash.

[21] Appl. No.: 533,675

[22] Filed: Sep. 26, 1995

Related U.S. Application Data

[63] Continuation of Ser. No. 212,396, Mar. 11, 1994, abandoned, which is a continuation of Ser. No. 804,954, Dec. 11, 1991, abandoned, which is a division of Ser. No. 330,846, Mar. 29, 1989, abandoned, which is a continuation-in-part of Ser. No. 157,273, Feb. 17, 1988, Pat. No. 5,322,678.

[51] Int. Cl.$^6$ .................... A61K 39/395; C07K 16/00
[52] U.S. Cl. .................... 424/183.1; 424/178.1; 530/391.1; 530/391.7; 530/402; 530/410
[58] Field of Search ................ 424/1.49, 178.1, 424/183.1; 530/391.1, 391.7, 402, 410

[56] References Cited

U.S. PATENT DOCUMENTS

| 4,082,507 | 4/1978 | Sawyer ................ 8/94.11 |
| 4,545,885 | 10/1985 | Paston et al. ............ 424/92 |
| 5,322,678 | 6/1994 | Morgan et al. ............ 424/1.53 |

FOREIGN PATENT DOCUMENTS

| 0217577 | 4/1987 | European Pat. Off. . |
| 0268707 | 6/1988 | European Pat. Off. . |

OTHER PUBLICATIONS

Waldmann, T.A., Science, 252:1657–1662, 1991.
Trovet et al, PNAS 79, 1982 pp. 626–629.
Vogt et al, Kidney International, 22, 1982, pp. 27–35.
Mennik et al, J. Immunol. 38 (11) 1987, pp. 4209–4217.
Ulloc.–Ayvirie et al, Human Reproduction 3(4) 1988 (Aug.) pp. 491–501.
Wacbsmotle et al, Res. J. Reticuloendothel, Soc. 24 (3) 1978, pp. 227–241.
Holcenberg et al., J. Biol Chem. 250 (11) 1975, pp. 4165–4107.
Vogt, Arnold, "Interaction of Cationized Antigen with Rat Glomerular Basemen Membrane: In Situ Immune Complex Formation," *International Society of Nephrology*, 27–35, 1982.

*Primary Examiner*—Toni R. Scheiner
*Assistant Examiner*—Susan Ungar
*Attorney, Agent, or Firm*—Seed and Berry LLP

[57] ABSTRACT

There is disclosed charge-modified conjugates comprising a targeting protein bound to a therapeutic or diagnostic agent. Charge-modifying a conjugate to cause an acidic shift in the isoelectric point results in prolonged serum half-life upon in vivo administration and is useful to accumulate a therapeutic agent at the target site. Conversely, charge-modification to cause a basic shift in the isoelectric point of the conjugate reduces serum half-life upon in vivo use for diagnostic imaging purposes and results in higher target-to-background ratios.

11 Claims, 5 Drawing Sheets

γ 2b

γ 2a

γ 1

ALTERATION OF PHARMACOKINETICS OF PROTEINS BY CHARGE MODIFICATION

This application is a continuation of application Ser. No. 08/212,396, filed Mar. 11, 1994, now abandoned, which is a continuation of application Ser. No. 07/804,954, filed Dec. 11, 1991, now abandoned, which is a divisional of application Ser. No. 07/330,846, filed Mar. 29, 1989, now abandoned, which is a continuation-in-part of application Ser. No. 07/157,273, filed Feb. 17, 1988, now U.S. Pat. No. 5,322,678.

TECHNICAL FIELD

The present invention relates to proteins and conjugates with charge modifications that affect their pharmacokinetic properties and immunogenicity upon in vivo administration. The charge modifications are manifest by changes in the isoelectric points of the protein, antibody or antibody fragment moiety of the conjugate or conjugated protein.

BACKGROUND OF THE INVENTION

Prior to describing the background of the invention, it is helpful to define certain terms which are used throughout this specification.

Conjugate: The term "conjugate" applies to any composition that comprises a targeting moiety, such as a biologic response modifier (BRM), (including lymphokines, interferons, erythropoietin, and colony stimulating factors) peptide hormones, antibody or antibody fragment, preferably a monoclonal antibody or monoclonal antibody fragment, and an effector moiety such as a radionuclide, toxin, drug, fibrinolytic enzyme or BRM molecule. The effector moiety can be attached to the targeting moiety either directly or through a linking group, ligand (e.g., bifunctional chelating agent), or a carrier molecule (e.g., albumin, dextran, poly-1-lysine).

Antibody Fragment: An antibody fragment comprises the specific binding regions of the antibody molecule corresponding to the variable and first constant regions on heavy and light chains. Examples of antibody fragments include F(ab')2, Fab' and Fab fragments. An antibody fragment can also include only the variable regions (Fv). Antibody fragments may also include chimetic molecules wherein constant regions of the antibody are substituted with constant regions of immunoglobulin from a different species.

Immunogenicity: Immunogenicity is a measure of the ability of a targeting protein or therapeutic moiety to elicit an immune response (humoral or cellular), when administered to a host. The present invention is concerned with the immunogenicity of the conjugates and their component parts.

Targeting Protein: In this specification a targeting protein is defined as a protein which is capable of binding to a cellular target or other target site, including but not limited to: antibodies and fragments thereof; lymphokines such as IL-1, 2, 3, 4, 5, and 6; $\alpha$, $\beta$, and $\gamma$ interferon; erythropoietin; colony stimulating factors such as G-CSF, GM-CSF and M-CSF; other biologic response modifiers and peptide hormones such as melanocyte stimulating hormone (MSH), follicle stimulating hormone (FSH), leutenizing hormone (LH), and human growth hormone (HGH); fibrinolytic enzymes and serum proteins (e.g., low density lipoproteins).

Serum Half-Life: Serum half-life is a time point at which half of the administered amount of targeting protein or conjugate thereof remains in the serum or plasma. Serum determinations over a series of time points can generate a curve which is useful for determining whole body exposure to an agent.

The advent of recombinant DNA and monoclonal antibody technologies has spawned a renewed interest in proteins that may have pharmaceutical applications. These technologies have made possible, for the first time, the large-scale production of substantially purified, homogeneous proteins with little lot-to-lot variation. Protein molecules such as interleukin-2, tissue plasminogen activator, human insulin, atrial naturetic peptide, interferons, monoclonal antibodies to tumor-associated antigens, and to effector cell subsets and fragments and conjugates thereof, have either received marketing approval in the United States or are currently undergoing multisite clinical trials.

In particular, there has been considerable interest in the "magic bullet" approach to cancer therapeutics using monoclonal antibodies conjugated to drugs, toxins, radionuclides and biological response modifiers. More recent efforts have been devoted to the conjugation of cytotoxic or antineoplastic drugs to specific antibodies, such as monoclonal antibodies, to produce conjugates which can selectively target tumor cells while sparing normal tissues.

A large number of different classes of agents have been considered. These agents include beta- and alpha-emitting isotopes, plant and bacterial toxins, and a variety of antineoplastic drugs, including intercalating agents, antimetabolites, alkylating agents and antibiotics. It is desirable to conjugate chemotherapeutic drugs to targeting molecules such as antibodies to decrease their toxicity directed toward normal tissues.

Conjugates of radioisotopes, drugs and toxins, as well as biologic response modifiers, may be potentially useful in the treatment of cancer and autoimmune diseases, and in the abrogation of transplant rejections. Each class of agent conjugated to an antibody provides conjugates having properties which may be useful for the treatment and diagnoses of cancers and other diseases, but each type also has potential drawbacks.

Radiotherapeutic conjugates, for example, are limited by the low dose of antibody that reaches the tumor and by the sensitivity of the bone marrow to the radiation dose absorbed from the circulating levels of antibody. Toxin conjugates are often potent cytotoxic agents, but suffer from rapid serum clearance usually by the liver. This results in poor tumor delivery. Conjugates formed with cytotoxic drugs are usually of lower potency than toxin conjugates. However, cytotoxic drug conjugates are extracted less rapidly by the liver and reticuloendothelial system (RES), resulting in improved tumor delivery properties.

Similarly, molecules such as tissue plasminogen activator (TPA) and interleukin-2 (IL-2) and some of the interferons have characteristic short serum half-lives. This results in decreased bioavailability for target tissue and, in some instances, increased toxicity. The common problem affecting all four types of conjugates is the limitation of the effective dose of the cytotoxic agent (radionuclide, toxin or drug) attached to the antibody or targeting protein that reaches the tumor site or receptor on potential effector cells.

It has been a goal of therapy and diagnostic imaging with conjugates to increase bioavailability of the circulating conjugate to the tumor site(s). Nonspecific binding of the conjugate to normal cells can occur by nonspecific interactions of the antibody, or agents conjugated to the antibody. Nonspecific binding of the antibody components can occur with cells of the RES tissue. An antibody's Fc region can interact with receptors both for Fc and complement components bound to antibody. One method that has been developed to reduce nonspecific interactions of antibody with RES cells is by treatment of the conjugate with an amphipathic molecule, such as an anionic surfactant, as disclosed in U.S. patent application Ser. No. 767,493, filed Aug. 20, 1985, and now abandoned. The entire disclosure of this patent application is hereby incorporated by reference.

Another method for increasing bioavailability of an conjugate is disclosed in U.S. patent application Ser. No. 917,176, filed Oct. 9, 1986, and now abandoned. The entire disclosure of this patent application is hereby incorporated by reference. As disclosed in U.S. patent application Ser. No. 917,176, an irrelevant antibody or conjugate is pre-injected, thereby swamping the mechanism(s) of nonspecific uptake of the pharmaceutically active conjugate.

Another method whereby nonspecific interactions of the conjugates with the Fc receptor can be minimized is to remove the Fc portion of the antibody with a proteolytic enzyme to create an antibody fragment as the targeting moiety of the conjugate. The use of an antibody fragment as the targeting agent still does not eliminate the problems of nonspecific interactions and binding of the conjugate to normal cells. As an example, in order to increase the sensitivity of radionuclide/antibody imaging, investigators have injected radiolabeled antibodies intralymphatically to detect disease bearing lymph nodes. Despite success in animal models, the method has not been of use in man because of nonspecific accumulation of radiolabel in both diseased and nondiseased lymph nodes. To overcome this nonspecificity, antibody fragments were produced and administered by this route for detection of malignant melanoma. Irrelevant, as well as relevant, Fab antibody fragments showed enhanced accumulation in tumor-involved nodes and less uptake in noninvolved nodes following subcutaneous or intralymphatic administration. (Nelp et al., "Preliminary Studies of Monoclonal Antibody Lymphoscintigraphy in Malignant Melanoma," *J. Nucl. Med.* 28:34–41, 1987.) Thus, even antibody fragments can undergo nonspecific interactions when administered by the intralymphatic route.

Nonspecific binding to normal cells by the conjugate can be further reduced by understanding the nature of the nonspecific binding. For example, the nonspecific binding of a radiolabeled antibody is increased by the use of radionuclides/chelate systems in which the chelate is not stable enough not to allow leaching of the radiolabel. For example, DTPA, a commonly used chelate for Indium-111 (In-111), does not bind In-111 avidly enough, allowing the leaching (e.g., 10%/day) from the radioconjugate. Free In-111 can then bind to transferrin and then the transferrin binds to receptors in RES tissues. The use of radionuclides can be improved by the use of more stable chelate systems as well as the use of radionuclides that are rapidly excreted upon dissociation from the conjugate.

Conjugates useful for cancer therapeutic purposes will require multiple administrations. Since the targeting protein of the conjugate is a monoclonal antibody or monoclonal antibody fragment of murine (mouse) origin, a host immune response will be generated against the antibody or the agent conjugated to the antibody. Nonspecific uptake into normal tissues, especially RES tissues, through any reception mediated mechanism, would result in catabolism of the conjugate to peptides by macrophages with presentation to immunocompetent T-cells and B-cells. These peptides could then be recognized by T-cell dependent or independent mechanisms and an antibody response generated. Conjugation of toxins or drugs to antibodies, which increase liver accumulation, would also enhance the immunogenicity of both the antibody and the agent conjugated to antibody. Generation of antibodies to components of the conjugate can lead to further nonspecific uptake of circulating conjugate into certain organs, especially RES tissue. Thus, biodistribution, serum clearance, normal organ accumulation, and excretion all impact the degree of immunogenicity of the conjugate and the ability to give multiple administrations to the patient.

Conjugates are not the only proteins useful for targeted imaging or therapy. Lymphokines like IL-2; $\alpha$, $\beta$, and $\gamma$ interferon, all termed "biologic response modifiers (BRMs)"; as well as TNF (tumor necrosis factor); and TPA (tissue plasminogen activator), share common features of requiring in vivo administration to target intra or extravascular receptors. These proteins can be removed from the circulation by either binding to cellular receptors or by excretion/catabolism. It is difficult to estimate what process accounts for the largest amount of protein removed from the circulation, however, modification of the protein to reduce receptor binding is not feasible since that may also reduce its effect or function. Thus, modification of excretion/metabolism may represent the best means for increasing serum half-life of these agents.

This has been recently addressed for TPA, an agent useful for blood clot lysis and imaging. The serum half-life of TPA was increased by producing a mutant protein by recombinant methods which had glycosylation sites and then producing the mutant in eukaryotic cells (Lau et al., *Biotechnology* 5: 953, 1987). Lau et al. showed that, in addition to increased serum half-life, lower doses of TPA were required to give the same in vivo fibrinolytic activity as nonglycosylated TPA. Glycosylation has been shown previously with many proteins to effect metabolism and excretion.

Thus, the ability to increase the serum half-life of proteins administered in vivo can have substantial impact on the efficacy and therapeutic index of such proteins. Therefore, a method is needed to reduce the nonspecific uptake and excretion of these protein molecules, thereby improving their serum half-lives and thus their availability for target tissues.

OBJECTS AND SUMMARY OF THE INVENTION

A general object of the present invention is to eliminate or substantially alleviate the above-noted problems in the prior art.

A more specific object of the invention is to increase the uptake of targeting proteins in general and conjugates, in particular, onto target tissues by reducing nonspecific accumulation, metabolism and excretion of conjugate.

An object of the invention is to reduce the immunogenicity of conjugates, especially conjugates made from murine-derived monoclonal antibodies or fragments, such that the conjugate can be administered to a patient multiple times without a strong host immune response against the conjugate.

An object of the invention is to increase the half-life of a therapeutic conjugate and thereby increase target site accumulation. Conversely, for a different purpose the half-life of a conjugate for imaging can be decreased by increased kidney uptake to achieve high target-to-background ratios at early time points.

A further object of the invention is to improve the serum half-lives, and thus availability for target tissues of other pharmaceutically active proteins and peptides such as interferons, interleukins, tissue plasminogen activators and hormones.

The above-identified objects of the invention are accomplished by modification and/or selection of antibodies and fragments thereof, biologic response modifiers, other targeting proteins, and conjugates with an appropriate isoelectric point and net charge. If the native targeting protein molecule does not have the desired isoelectric point, charge modifications can be made by the conjugation of lysine amino groups or gamma carboxylates on the antibody protein molecule with reagents such as succinic anhydride, ethylene diamine, via 1-ethyl-3-(diamethylaminopropyl)-carbodiimide (ECDI).

The result of charge modification of the targeting protein such as an antibody or antibody fragment or biologic response modifier on a conjugate is an alteration of serum half-life by a minimum factor of at least 10%. Preferably, conjugate serum half-life is increased or decreased (depending upon the isoelectric point shift) by a factor of approximately 50%. Similarly, charge modification of other biologic response modifier targeting proteins such as lymphokines, TPA and TNF, can produce an increased serum half-life for the charge-modified protein, resulting in the higher availability for their targeted receptors or acceptors.

DETAILED DESCRIPTION OF THE INVENTION

Figure 1A:
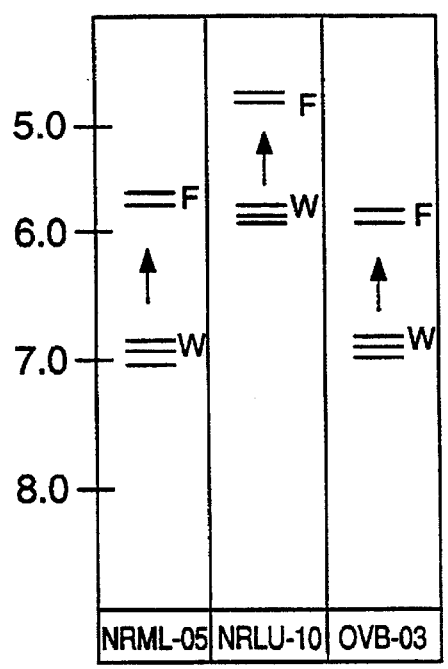
FIG. 1 indicates the isoelectric point (pI) shifts with several antibodies and antibody fragments. Antibodies and their fragments were evaluated for pI on a pH 3–10 isoelectric focusing gel. Figure legends are: W=whole monoclonal antibody; $F'=F(ab')_2$; and F=Fab or Fab'.

Briefly stated, in the present invention, the in vivo pharmacokinetics and immunogenicity of proteins and conjugates thereof are controlled.

The proteins generally are targeting proteins. The term "targeting protein," as used herein, refers to proteins which are capable of binding to a desired target site in vivo. The targeting protein may bind to a receptor, substrate, antigenic determinant, or other binding site on a target cell or other target site. Examples of targeting proteins include, but are not limited to, antibodies and antibody fragments; serum proteins; fibrinolytic enzymes; peptide hormones: and biologic response modifiers. Among the suitable biologic response modifiers are lymphokines such as interleukins (e.g., IL-1, IL-2, IL-3, IL-4, IL-5, and IL-6) or interferons (e.g., α, β, and γ interferon), erythropoietin, and colony stimulating factors (e.g., G-CSF, GM-CSF, and M-CSF). Peptide hormones include melanocyte stimulating hormone, follicle stimulating hormone, lutenizing hormone, and human growth hormone. Fibrinolytic enzymes include tissue-type plasminogen activator, streptokinase, and urokinase. Serum proteins include human low density lipoproteins.

These proteins may be modified to produce variants, analogs and fragments of the proteins, so long as the desired biological properties (i.e., the ability to bind to the target site or the ability to have the same effector activity as the parent unmodified protein) is retained. The proteins may be modified by using various genetic engineering or protein engineering techniques.

Kidney clearance and metabolism and liver clearance and metabolism of immune complexes and conjugates can be affected by the charge of the immune complex or conjugate. There exist negative charges on the renal glomerular basement membrane consisting of patches of proteoglycan. These proteoglycan molecules can interact with cationic antigen molecules complexed with antibodies. Cationic molecules of 900,000 molecular or greater will not pass through the lamina densa. See Mannik et al., "Immune Complexes with Cationic Antibodies Deposit in Glomeruli More Effectively Than Cationic Antibodies Alone," *J. Immun.* 38: 4209–17 (1987). The binding of a protein to glomeruli increases with the increasing (more basic) isoelectric point of the immune complex. See Vogt et al., "Interaction of Cationized Antigen with Rat Glomerular Basement Membrane: In Situ Immune Complex Formation," *Kidney Int.* 22:27 (1982). The negative charges located on the glomerular basement membrane can potentially undergo charge interactions with antibody molecules whether complexed with antigen or not although deposition is enhanced by complexation with antibody.

Because antibody fragments are more likely to enter the kidney filtration system at a faster rate than whole antibodies, they will be capable of undergoing charge interactions with the glomerular basement membrane more readily. Further, the more cationic antibody or fragments are more readily deposited in the glomerular basement membrane than a more anionic antibody or fragment. A consequence of rapid renal clearance associated with the deposition of cationic antibody molecules onto the glomerular basement membrane is a rapid serum clearance and decreased serum half-life. This relationship is surprising in view of prior teachings in the art. A molecule, such as an conjugate, that effectively binds in the kidney is removed from the circulation at a more rapid rate than an conjugate that would bind in the kidney with relatively low affinity. Therefore, the serum half-life of a conjugate is decreased if the conjugate is selected or modified to be more cationic, and increased if the conjugate is selected or modified to be more anionic.

Similarly, there may exist other clearance mechanisms in the liver which are able to recognize charged molecules and more rapidly effect a binding of excretion through the hepatobiliary system.

Figure 1B:
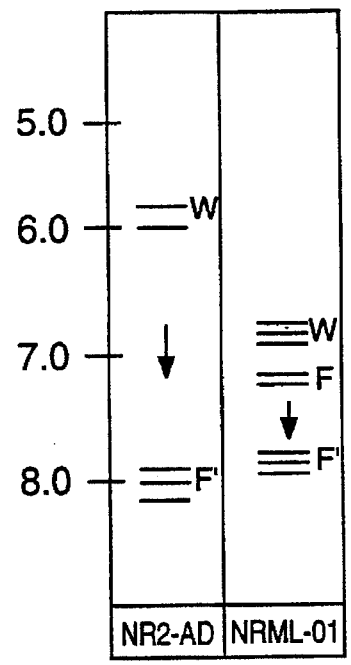
Figure 1C:
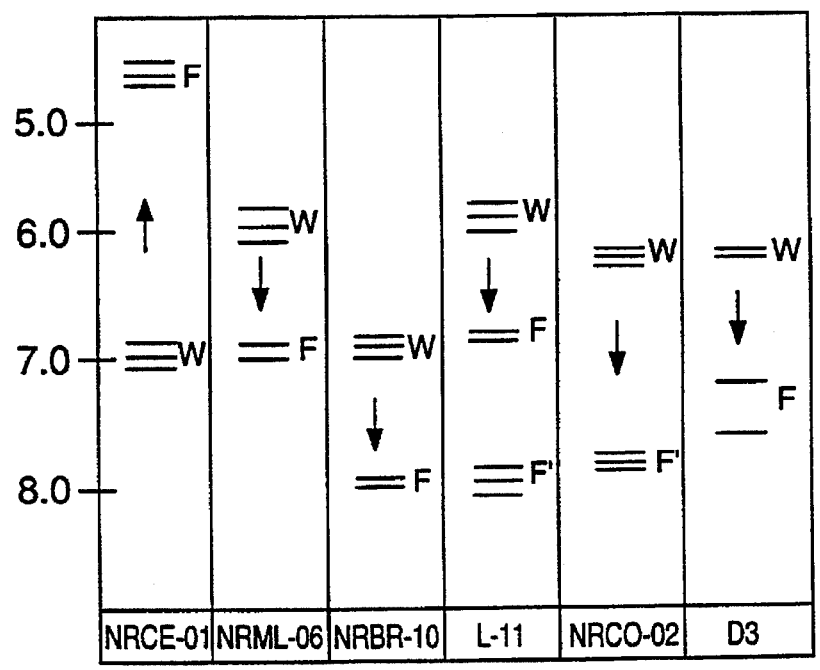

The present invention has demonstrated the relationship between serum half-life and excretion with charge of antibodies and fragment thereof. Most antibodies and fragments have neutral or basic pI, inappropriate for long serum half-lives and therefore require modification to impart a more appropriate net charge. As an example, monoclonal antibodies and monoclonal antibody fragments have characteristic isoelectric points and characteristic changes in isoelectric points following proteolytic enzymatic fragmentation into antibody fragments. Examples of the changes in isoelectric points are shown in FIG. 1.

Typically, fragments are basic compared to whole antibody. A specific exception was the NR-CE-01 antibody which underwent an acidic shift after fragmentation. A general exception is with antibodies of the γ2b subclass which undergo an acidic shift upon fragmentation. Regardless of the subclass, monoclonal antibody fragments can be classified as neutral, basic or acidic. The NR-CE-01 antibody formed a third category of a highly acidic fragment.

Therefore, an conjugate using an antibody fragment, as compared with the parent whole antibody as the targeting moiety, will demonstrate more kidney localization, a shorter serum half-life, and better tissue/blood ratios if used for diagnostic imaging purposes. See FIG. 1. Antibody fragments have faster serum clearance through an enhanced ability to bind to anionic sites in vivo in the glomerular basement membrane of the kidney as well as to be excreted directly without binding.

Figure 2:
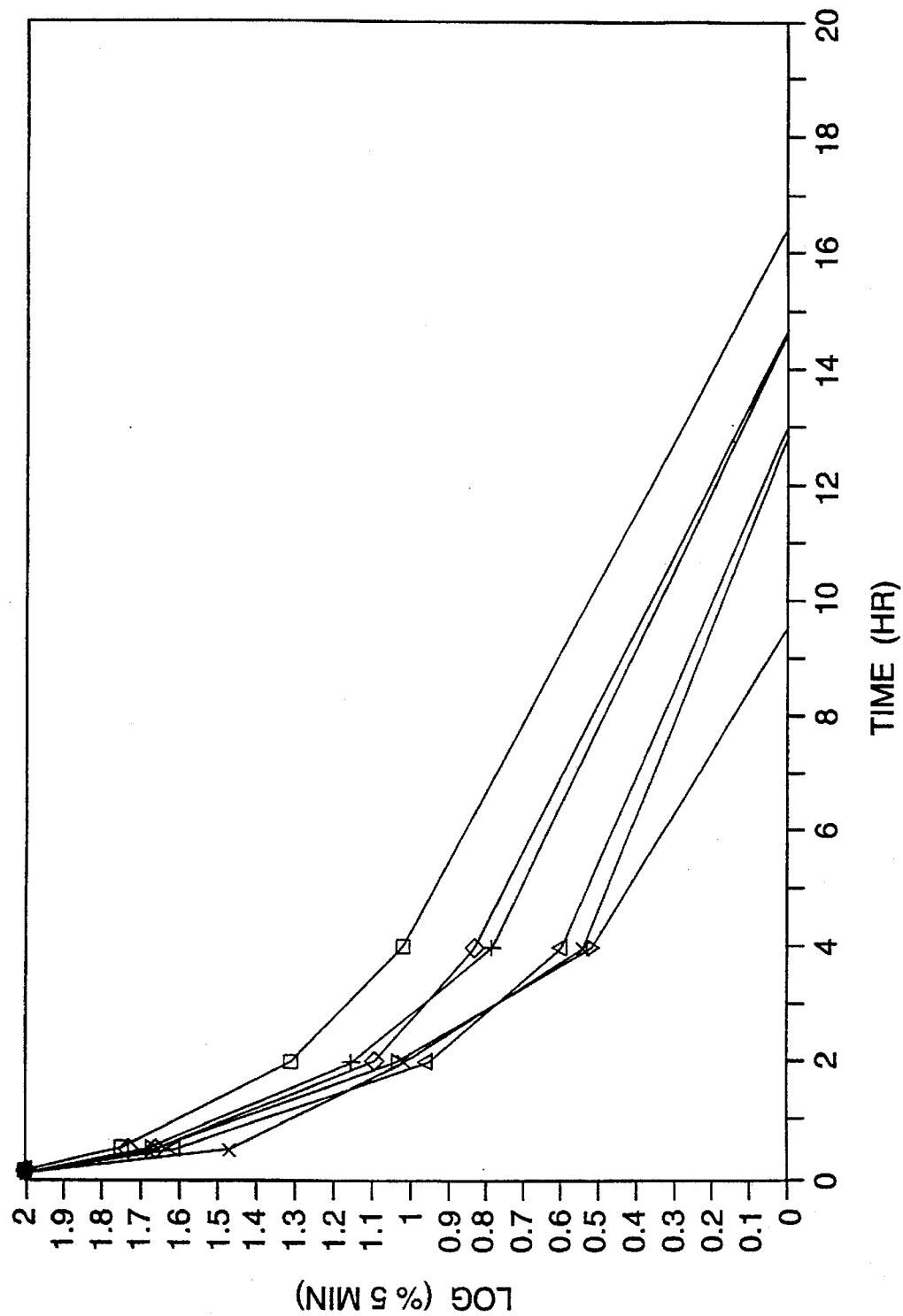
FIG. 2 illustrates the serum clearance rates of several antibody fragments. Fab or Fab' fragments of certain antibodies with different pI values (see FIG. 1) were radiolabeled and injected into Balb/c mice. Blood was withdrawn by retroorbital puncture at the indicated times. The figure legends are: □ is NR-CE-01; ◊ is NR-LU-10; + is NR-ML-05; Δ is D3; X is NR-ML-01 and ▽ is NR-ML-06.

As shown in FIG. 2, antibody fragments with more acidic isoelectric points have slower serum clearance rates (i.e., increased serum half-life) than those with neutral or basic pI. Just as there were three categories of antibody fragments with regard to isoelectric point, there are three categories of fragments with regard to clearance rates. The neutral or basic fragments clear the fastest and acidic fragments more slowly. A highly acidic fragment like NR-CE-01 is rarely encountered. An antibody fragment with an acidic isoelectric point is a preferred targeting agent for conjugates with therapeutic applications, where prolonged serum half-life to allow for greater target site localization is preferred. Therefore, the invention provides for a process to determine the preferred targeting moiety of a conjugate based upon its isoelectric point and the desired serum half-life properties of the conjugate.

As a second aspect of this invention, the targeting proteins and/or conjugates thereof can be charge-modified to have a more appropriate serum clearance rate, depending upon the intended use of the conjugate. Whether one uses reagents which cause a basic or acidic shift of the isoelectric point depends upon the application of the conjugate. For example, a conjugate used for diagnostic imaging purposes needs a neutral or basic antibody fragment for increased serum clearance and for high tumor-to-background ratios at early time points. This can be a natural property of the fragment or can be imparted by charge modification. A more basic fragment is preferable for short half-life isotopes like Tc-99m (technetium) and I-123 (iodine), with 6- and 13-hour half-lives, respectively. Longer half-life isotopes like Cu-67 (2.4d), Ga-67 (5.2d), Ga-68 (68 min.), Zr-89 (3.3d), In-111 (2.8d), I-131 (8.1d), Ru-97 (2.9d), Pb-203 (2.2d), and Sn-177m (14d) can utilize more acidic fragments.

For therapeutic applications a long serum halflife is desired to allow increased localization to the target site and to increase the useful portion of the administered dose of a conjugate. For radiotherapeutic, drug, or toxin conjugates, it is desirable to administer a greater total dose to the localized target site without concentration of conjugate within specific organs. This is accomplished by modifying the charge of the antibody, antibody fragment and/or conjugate to have a more acidic isoelectric point with an acid shift of at least one-tenth of a pH unit and no more than four pH units. Preferably, the isoelectric point acidic shift is approximately one pH unit. At a pI of 4.0 or lower (more acid), virtually all ionizable groups are protonated in the protein. The more anionic conjugate will have less renal retention and hepatobilliary excretion and stay in the circulation longer, resulting in increased tumor delivery. This is accomplished by charge modifying at least one lysine residue in the targeting protein from a net positive charge to a net negative charge.

Charge-modification of the targeting protein and/or the conjugate is accomplished by treatment with an anion-forming or a cation-forming reagent. Recombinant DNA technology may also be used to produce a protein with more or less lysine and glutamic acid residues than the native molecule. The targeting protein can be treated either before or after formation of the conjugate, or at both times.

The charge-modifying reagents in general comprise a functional group which will react with the desired amino acid either directly or indirectly (e.g., through a carbodiimide coupling reagent), as well as a charged ionic group, either positively or negatively charged.

In one embodiment of the invention, the charge-modifying agent is of the formula:

X—G—Y wherein X represents a functional group that reacts with an amino acid on a protein to be charge-modified, or a precursor of such a functional group. The reactive X group may be generated from a precursor during the reaction of the charge-modifying agent with the protein. Y represents a charged group (e.g., an inorganic ion) or a precursor thereof. When Y is a precursor, the charged group is generated during reaction of the charge-modifying agent with the protein. The charge-modifying agent is an anion-forming agent when Y confers a net negative charge on the modified amino acid. The charge-modifying agent is a cation-forming agent when Y confers a net positive charge on the modified amino acid. G represents an optional spacer between the X and Y groups and may be chosen from aliphatic, alkene, or aromatic organic groups, for example. When G is an aliphatic group, such as a methylene chain, the G group preferably comprises less than 6 carbon atoms.

When the charge-modifying agent is an anion-forming agent, the X group may react with primary amines on lysine residues of the protein to be charge-modified. Examples of X groups which will react with lysine residues include active esters (both carboxylic and imide esters), maleimides, and anhydrides. Among the preferred active esters are N-hydroxysuccinimidyl, thiophenyl, 2,3,5,6-tetrafluorophenyl, and 2,3,5,6-tetrafluorothiophenyl esters. In addition to reaction of lysines with anion-forming agents, an acidic shift in the PI of a targeting protein may be effected by derivatization of arginine residues (with glyoxal, phenyl glyoxal, or cyclohexonedione, for example).

Among the many negatively charged groups which may be used as Y groups are phosphates, phosphonates, sulfates, nitrates, borates, silicates, carbonates, and carboxyl groups. An example of a Y group which may be generated during the reaction of the anion-forming agent with the protein is a carboxyl group generated from an anhydride.

Useful anion-forming agents include but are not limited to compounds comprising an anydride and/or at least one COOH group, such as succinic anhydride, other cyclic acid anhydrides, phthalic anhydride, maleic anhydride, N-ethyl maleimide substituted with carboxyl groups, aliphatic anhydrides (e.g., acetic anhydride), aromoatic anhydrides, pH-reversible anhydrides (e.g., citraconic anhydride and dimethyl maleic anhydride), alpha halo acids such as bromoacetate and iodoacetate, and diacids or triacids substituted with one of the above-described X groups. One example of a diacid substituted with an X group is the compound of the following formula:

$$\begin{array}{c}\text{O} \\ \parallel \\ \diagup \\ \diagdown \\ \text{N-O-C-CH}_2\text{CH}_2\text{-S-CH(COOH)-COOH} \\ \diagup \\ \parallel \\ \text{O}\end{array}$$

in which the X group is the N-succidimidyl ester. Other anion-forming reagents are tri- and tetracarboxylic acid anhydrides, e.g., aconitic, benzene tetracarboxylic, pyridine tetracarboxylic, napththalene tetracarboxylic, and norbornene dicarboxylic anhydrides.

One group of charge-modifying agents is derived from sugars which have charged groups attached thereto. Sugar molecules having inorganic ions attached thereto are commercially available (e.g., glucose-6-phosphate). A suitable functional group for reaction with an amino acid (i.e., the above-described X groups) may be attached to such compounds. Alternatively, the charge modifying agent may be attached to the protein by non-enzymatic glycosylation reactions. An example of charge modification using such a sugar-derived, anion-forming reagent is presented in Example 8 below.

Useful cation-forming agents include ethylene diamine via an EDCI reaction with carboxyl groups of the antibody. Other useful cationic agents include triethylene tetraamine, 4-dimethylamino butylamine, N,N-dimethylaminoethyl amine, and dimethylamino benzaldehyde. The cationic reagents will modify a glutamic acid or aspartic acid amino acid of the targeting protein from a negative charge to a positive charge with a net change of +2. Thus the invention encompasses the charge-modified targeting protein wherein at least one glutamic acid or aspartic acid amino acid residue is charge-modified to a net positive charge. The basic shift of the isoelectric point is at least one-tenth of a pH unit and not more than four pH units. Preferably, the basic isoelectric point shift is approximately one pH unit.

Preferably, the use of succinic anhydride can impart negative charges to a protein molecule. For each lysine residue that gets modified, there is a net change of two charges. When the charged group on an anion-forming reagent is a phosphate or a sulfate, a net change of −3 in the charge is realized for each lysine residue that is modified. Therefore, dramatic shifts in the isoelectric point of an antibody or conjugate may be accomplished with only minimal lysine modification.

As discussed above, targeting proteins or conjugates thereof may be reacted with anion- or cation-forming reagents to effect charge modification. Certain therapeutic polypeptides, e.g., toxins, have properties that adversely affect the biodistribution of conjugates prepared therefrom. For example, the toxin may bind to receptors on normal cells. Thus it may be advantageous to charge-modify the therapeutic polypeptide as well as (or instead of) the targeting protein, either separately (before conjugate formation) or by treating the entire conjugate with an anion-forming agent.

Examples of polypeptide toxins include the holotoxins abrin, ricin, diphtheria toxin, Pseudomonas exotoxin (PE), and fragments thereof. Receptors for these toxins on normal tissues cause uptake of conjugates prepared therefrom into tissues such as the liver. The result is undesirable toxicity toward normal cells and diminished delivery of the conjugate to a desired target site.

One embodiment of the present invention involves treatment of a polypeptide toxin with one of the above-described anion-forming agents. The resulting modification of the lysines (including those in the cell-binding region) may diminish binding of the toxin to non-target cells, thereby increasing the serum half-life of the toxin or conjugates thereof. A higher percentage of conjugates comprising such a charge-modified toxin therefore may be delivered to the desired target site in vivo. PE is very lysine poor, except for the cell-binding domain, which contains 12 of the 35 lysine residues in the PE protein. Therefore, the anion-forming reagent will bind primarily to the cell-binding domain of the PE protein, and other domains (including the domain responsible for the enzymatic activity of the toxin) are only minimally modified. The resulting negative charge on the modified lysine residues in the cell-binding region may cause electronic repulsion between the charge-modified toxin and the receptor for the toxin on cell surfaces.

It is desirable to modify multiple lysine residues in a polypeptide toxin such as PE with an anion-forming reagent. The reduction of cytotoxicity appears to closely parallel the extent of derivatization. It has been found that derivatization of PE with about 8 or more succinyl groups (as a result of reaction with succinic anhydride) reduces its toxicity to colon carcinoma HT-29 cells by one log or more, as measured by in vitro cytotoxicity assays. Derivatization with about 12 or more succinyl groups reduces its toxicity by two logs or more. Binding of the toxin to cellular receptors therefore may be reduced by modification of multiple lysine residues. Undesirable binding of toxin-targeting protein conjugates to non-target cells via toxin receptors on the cells therefore also may be decreased.

The enzymatic activity of the toxin (needed for the desired therapeutic efficacy) is not diminished by the modification of lysine residues with the anion-forming reagent. Immunoconjugates comprising the charge-modified PE are capable of selectively killing target cells. The present invention thus provides a method of reducing toxicity of a polypeptide toxin or conjugates thereof toward non-target (e.g., normal) cells, comprising reacting the toxin or conjugate prepared therefrom with an anion-forming reagent. For Pseudomonas exotoxin, the anion-forming reagent preferably reacts with lysine residues of the toxin.

Charge-modified BRMs, conjugates or charge-modified antibodies or antibody fragments formed into conjugates are often administered intravenously. The charge modification of the antibody, antibody fragment and/or conjugate will also impart higher selectivity to conjugates with charge-modified antibodies or antibody fragments when administered via the intralymphatic or subcutaneous routes of administration. Within lymph vessels and lymph nodes, lymph fluid moves at a slower rate than blood within the intravascular compartment. Thus, it would appear that nonspecific interactions between conjugates and normal lymphatic tissue, which do not occur with intravenous administration, would be enhanced upon intralymphatic administration of the conjugate. This is due to the higher concentration of conjugates, antibody or antibody fragment maintained in the lymph node via intralymphatic administration.

Tumor cells generally have a net negative surface charge due to the fact that tumor cells have a higher degree of sialyted glycoproteins and glycolipids on their cell surface than normal cells. Normal cells similarly have clusters of negative charges on their membranes although they do not have the density of negative charges as do tumor cells. Therefore, imparting a net negative charge to an antibody or antibody fragment made into a conjugate will further decrease the tendency of the negatively charged conjugate to interact with negatively charged cell surfaces via antigen nonspecific means. The intralymphatic administration of a charge-modified antibody fragment incorporated into an conjugate will result in higher selectivity between tumor and non-tumor cells in tumor-involved lymph nodes.

There is a reduction in the elimination and/or metabolism of charge-modified conjugates made from targeting proteins comprising antibodies, antibody fragments and biologic response modifiers (see examples). By creating a more homogeneous distribution of negative charges on the surface of the targeting protein, nonspecific site accumulation is reduced. This directly reduces the ability of macrophages to metabolize and present peptides to immunocompetent cells. In addition, peptides with a more homogenous charge distribution are less recognized by T-cell dependent mechanisms similar to polymers with repetitive sequences which are less immunogenic. Thus, the lack of accumulation and processing, as well as homogeneity of charge, will lead to decreased immunogenicity.

Antibody reactivity to succinylated proteins has been previously assessed and found to be reduced with succinic anhydride. This requires, however, high levels of lysine modification (50% to 90%) of antigen, and unfolding of the protein due to charge repulsion. Preferably, the use of succinic anhydride at the preferred ratios of the inventive process results in approximately 10% or less of the available lysine residues becoming charge-modified. Immunogenicity of charge-modified proteins has not been previously determined.

Chimetic antibodies have been created by recombinant DNA technology. The chimetic antibodies may contain the constant regions of human heavy and light chains and the murine variable regions of both chains. Chimetic antibodies are expected to have reduced immunogenicity, but may evoke a greater percentage of antiidio-type responses. The selection or modification of the antibody moiety with an appropriate isoelectric point may similarly reduce the rate of anti-idiotype formation.

The following examples illustrate several uses of the inventive process and the novel conjugate and antibody compositions. The examples are offered by way of illustration and not by way of limitation.

EXAMPLE 1

Charge Modification—Acidic Shift

Succinic anhydride is dissolved in DMSO or another organic solvent at a concentration of 40 mg per 200 microliters. Succinic anhydride is then added to an antibody solution at molar ratios of succinic anhydride to protein of 1:5, 1:10 and 1:25. The reaction is carried out at room temperature for 15 minutes. After the reaction is completed, the succinic acid is removed by ultrafiltration (e.g., Amicon or Centricon) or by gel filtration through a G-25 column. The degree of isoelectric shift is determined by isoelectric focusing.

EXAMPLE 2

Charge Modification—Basic Shift

Positive charges are added to an antibody, antibody fragment and/or conjugate by adjusting the protein concentration to approximately 3 to 5 mg/ml with 0.125 molar sodium phosphate buffer at pH 5.0. EDCI is subsequently dissolved in water and added to the protein in different molar ratios, but generally between 1:300 and 1:10,000 (protein-to-EDCI ratio). The reaction generates activated carboxylates which are then subsequently conjugated with different molar ratios of ethylene diamine. The molar ratios usually range from 1:1,200 through 1:30,000 (protein-to-ethylene diamine ratio). The ethylene diamine solution is adjusted to a pH of approximately 5.0 with 0.125 molar phosphate buffer. The mixture is allowed to stir for approximately one hour at room temperature. After completion of the reaction, the unreacted material is removed by gel filtration through a G-25 column or by ultrafiltration. Characteristic shifts in the isoelectric point are determined by isoelectric focusing.

EXAMPLE 3

Effect of Succinic Anhydride Treatment on Immunoreactivity of Antibodies and Fragments Since the antibodies and antibody fragments of the present invention undergo lysine modification, the effect of the biochemical modification on the immunoreactivity and affinity of the antibody needs to be evaluated. A representative whole antibody and antibody fragment were assessed for their ability to bind, as radiolabeled antibodies, to target tumor cells. NR-CO-04 is an $IgG_3$ anti-colon carcinoma murine monoclonal antibody. NR-CO-04 was reacted with succinic anhydride in the ratios shown. As shown in Table 1, NR-CO-04, after charge modification with succinic anhydride, showed no significant change in the percentage of antibody molecules binding to target cells. The NR-CO-04 monoclonal antibody was assessed by incubation of radiolabeled antibody with cells at a concentration of 1.0 to $2.5\times10^6$ target cells at 37° C. for one hour. Separation of unbound antibody was effected by centrifugation through oil. The measure of binding was adjusted for radiolabeled antibody purity and nonspecific binding.

TABLE 1

Immunoreactivity of Succinylated Antibody as Assessed by Radiolabeled Binding

| | Binding | | Adjusted IR |
|---|---|---|---|
| Modification | S | NS | (%) |
| None | 57 | 01 | 57 |
| 1:5 | 55 | 03 | 53 |
| 1:10 | 63 | 13 | 51 |

S = specific plus nonspecifically bound counts; NS = nonspecifically bound counts in the presence of 100-fold cold competing antibody.

Similarly, the Fab fragment of NR-Ml-05, an anti-melanoma antibody, exhibited a retention of its immunoreactivity after charge modification with succinic anhydride. However, when both antibody forms were assessed by a competition ELISA against unmodified antibody, succinylated antibody or fragment was a more effective competitor, as shown in Table 2. In Table 2, succinylated antibody was titrated within the range of 1 μg to 10 μg/ml for binding to target cells. Biotinylated whole antibody, either NR-ML-05 or NR-CO-04 was added and the degree of competition was assessed. Competition was compared between modified antibody and non-modified antibody.

TABLE 2

Immunoreactivity of Succinylated Antibody as Assessed by Competitive ELISA

| AB | Form | Modification | IR (%) |
|---|---|---|---|
| NR-ML-05 | Fab | None | 100 |
| | | 5:1 | 157 |
| | | 10:1 | 161 |
| | | 25:1 | 94 |
| NR-CO-04 | IgG | None | 80 |
| | | 5:1 | 245 |
| | | 10:1 | 243 |
| | | 25:1 | 84 |

The data from Tables 1 and 2, when taken together, indicate that succinic anhydride treatment, especially within the parameters outlined above, does not alter the number of antibody molecules capable of binding to target antigen but enhances an antibody's ability to compete, thus indicating an increase in affinity.

EXAMPLE 4

Effect of Succinic Anhydride Treatment on Solubility and Effector Functions of Monoclonal Antibodies $IgG_3$ class murine monoclonal antibodies generally are potent mediators of antibody-dependent, cell-mediated cytotoxicity. Some murine monoclonal antibodies mediate killing with human complement. Murine monoclonal antibodies of the IgG3 subclass are generally poorly soluble, often precipitating upon storage at refrigeration conditions.

Succinic anhydride treatment, at low levels, did not modify the antigen binding capability of the monoclonal antibodies tested. The monoclonal antibody effector functions were also evaluated for the murine $IgG_3$. NR-CO-04, directed to colon cancer. Antibody effector functions include complement-mediated cytotoxicity (C'MC) and antibody-dependent, cell-mediated cytotoxicity (ADCC). The results of these evaluations are shown in Table 3. In Table 3, C'MC activity is identical for succinic anhydride-modified antibody versus unmodified control. Even at the highest ratios (1:25), there is no effect on the effector functions ADCC or C'MC.

TABLE 3

Effect of Succinylation on Antibody Effector Functions

| Modification | ADCC+ (%) | C'MC* (%) |
|---|---|---|
| None | 19.1 | 67.9 |
| 5:1 | N.D. | 61.0 |
| 10:1 | 18.9 | 69.5 |
| 25:1 | 19.1 | 69.2 |
| Control° | 20.4 | 74.1 |

°NR-CO-04 MAB control was treated under same conditions as succinylated antibody but succinic anhydride was omitted.
+Percent $^{51}Cr$ release upon incubation (37° C. - 4 hours) of normal donor mononuclear cells with target cells and NR-CO-04 MAB at 500 ng/well. Effector: target ratio = 25:1. Background release with effector and target cells alone was subtracted.
*Percent $^{51}Cr$ release upon incubation (37° C. - 1 hour) of NR-CO-04 MAB (500 mg/well) with target cells and 1:40 dilution of human AB serum as a complement source.

Therefore, the data from Examples 3 and 4 demonstrate that both immunoreactivity and effector functions appear to be preserved for charge-modified antibodies. Surprisingly, the resulting charged modified molecule demonstrated improved solubility with no concomitant decrease in immunoreactivity, ADCC or C'MC.

EXAMPLE 5

Effect of Succinic Anhydride Treatment on Serum Clearance and Tumor Delivery

Figure 3:
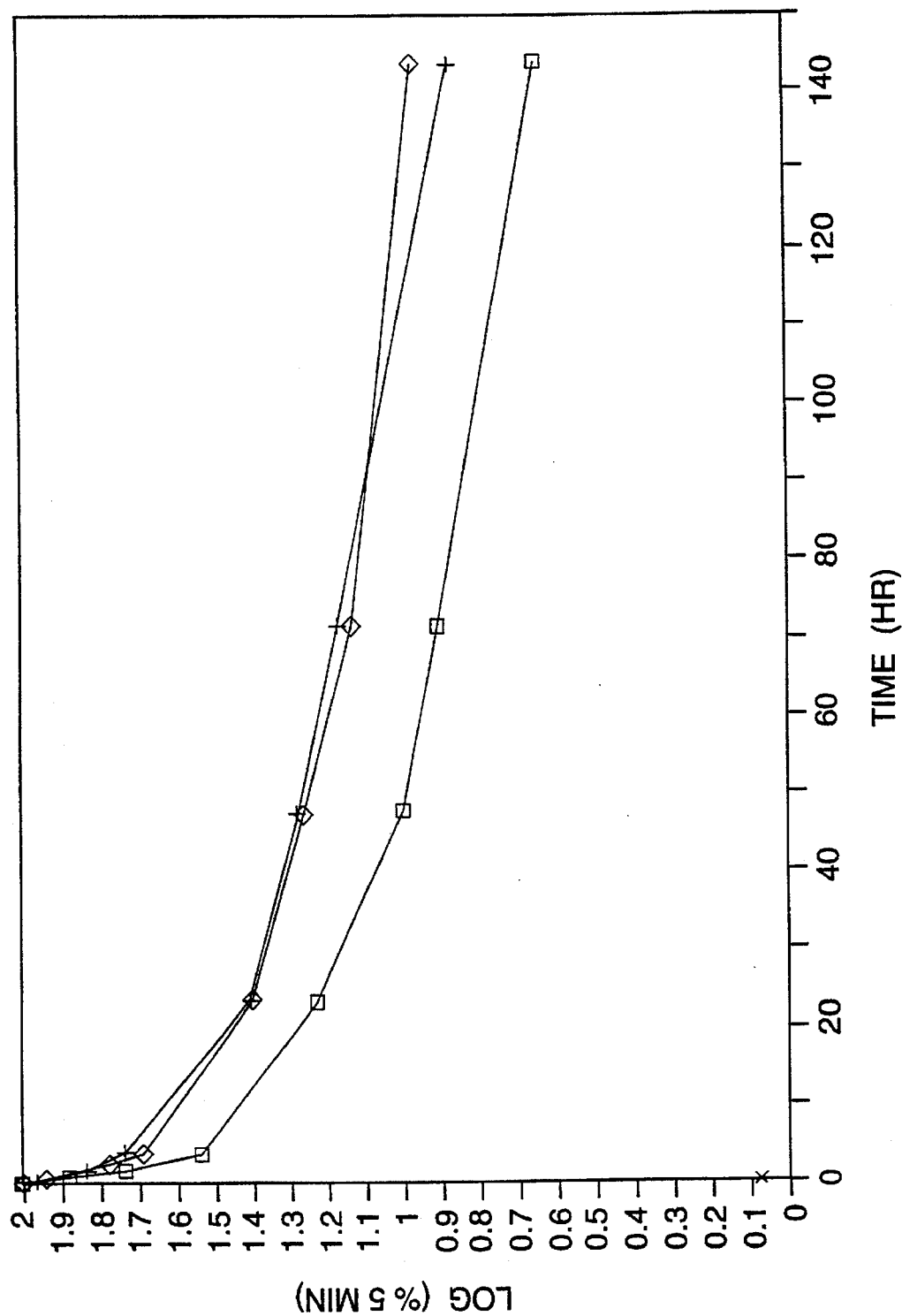
FIG. 3 illustrates the serum clearance of succinylated whole antibody. The NR-CO-04 monoclonal antibody was radiolabeled and assessed as in FIG. 2. Figure legends are: □ is unmodified NR-CO-04 monoclonal antibody; ◊ is NR-CO-04 modified with a 5:1 molar ratio (succinic anhydride: antibody); and + is 10:1 molar ratio charge modification. As is shown in FIG. 3, charge modification increases serum retention of the whole monoclonal antibody.

Administration of whole monoclonal antibody NR-CO-04 shows serum clearance typical of a whole antibody with a serum half-life of 24 hours. See FIG. 3. Upon modification of the antibody with a 1:5 or 1:10 offering of succinic anhydride, the serum half-life is greatly increased in both the alpha and beta phases of clearance.

Similar results are obtained by charge modification of F(ab')2 fragments of the anti-melanoma 9.2.27 monoclonal antibody, with a significant prolongation of serum half-life.

The Fab fragment of NR-Ml-05 is subjected to succinic anhydride treatment at a 101:1 and 25:1 offering. The percent of the dose of antibody fragment per gram accumulating into the tumor site is increased at the 20-hour sacrifice point with the 10:1 offering. See FIG. 4. Higher offerings of succinic anhydride with this monoclonal antibody fragment modifies the immunoreactivity of the antibody fragment, and this results in lower tumor accumulation of the fragment.

Figure 4A:
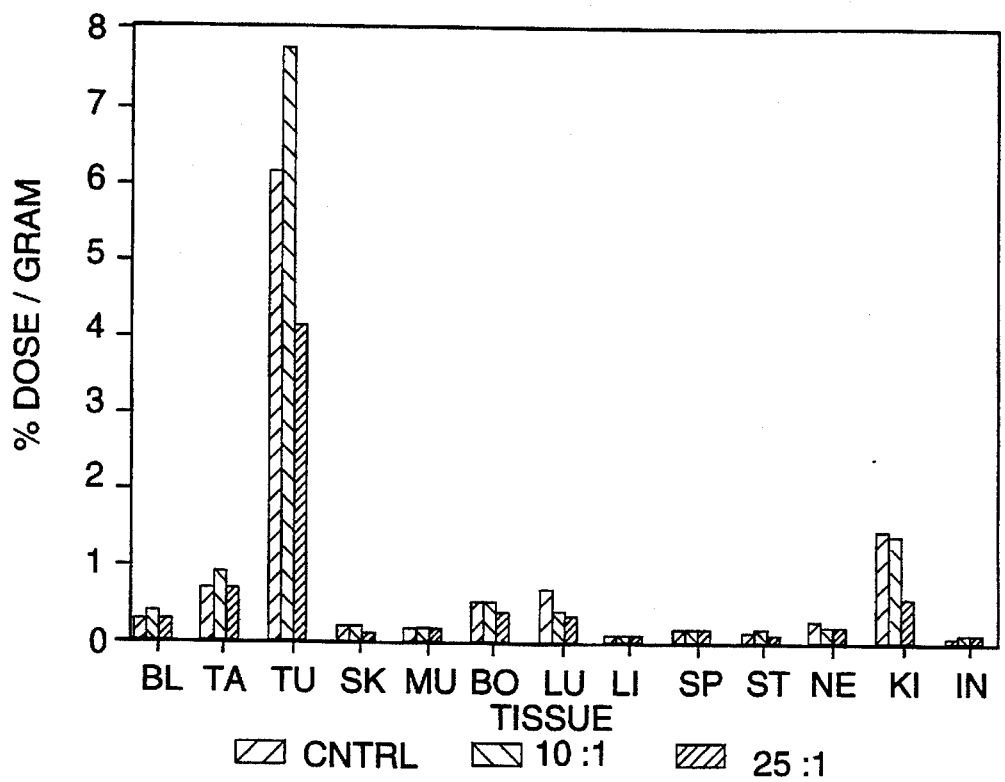
FIG. 4 is a whole animal biodistribution and tumor localization profile of succinylated monoclonal antibody fragment. The NR-ML-05 Fab was succinylated, radiolabeled and injected into target tumor bearing nude mice. Counts of various tissue and tumor were made at 20 hours post administration. Three molar ratios of succinic anhydride to antibody were included as indicated. The figure legends are: BL=blood; TA=tail; TU=tumor; SK=skin; MU=muscle; BO=bone; LU=lung; LI=liver; SP=spleen; ST=stomach; NE=neck; KI=kidney; and IN=intestine.
Figure 4B:
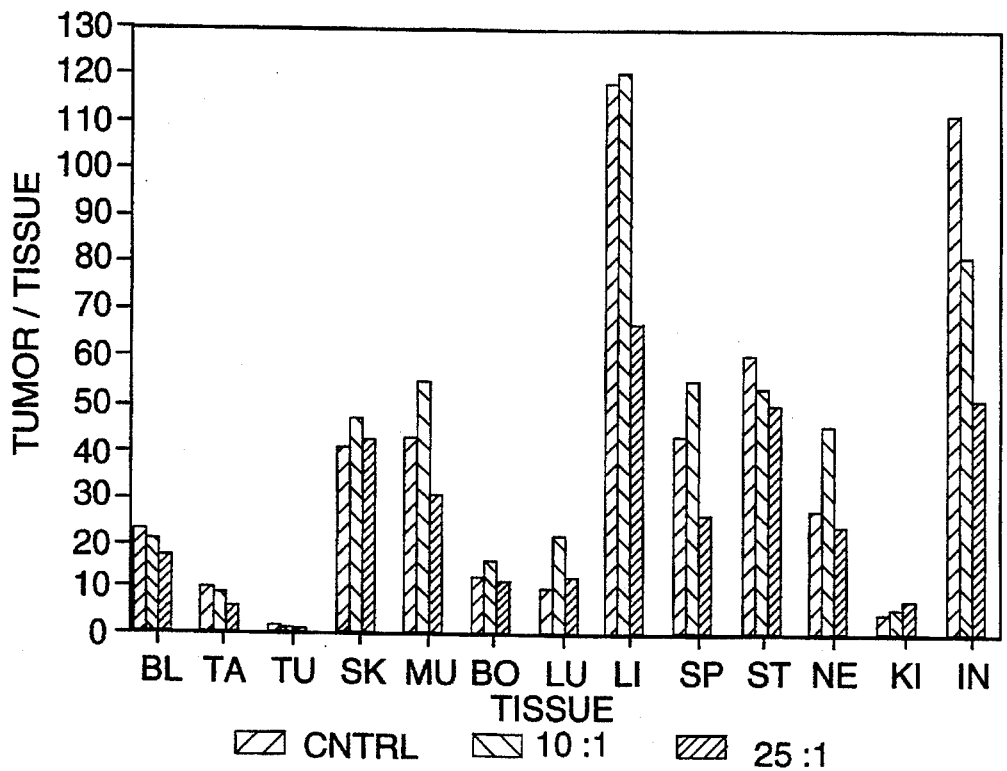

FIG. 4 also shows that tumor-to-blood ratios are nearly identical at the 20-hour time point for charge-modified and unmodified antibody fragments. This means that the total dose accumulated into the tumor is higher with the charge-modified antibody fragment. Similar results are obtained with the 9.2.27 F(ab')2 monoclonal antibody fragments.

Figure 5:
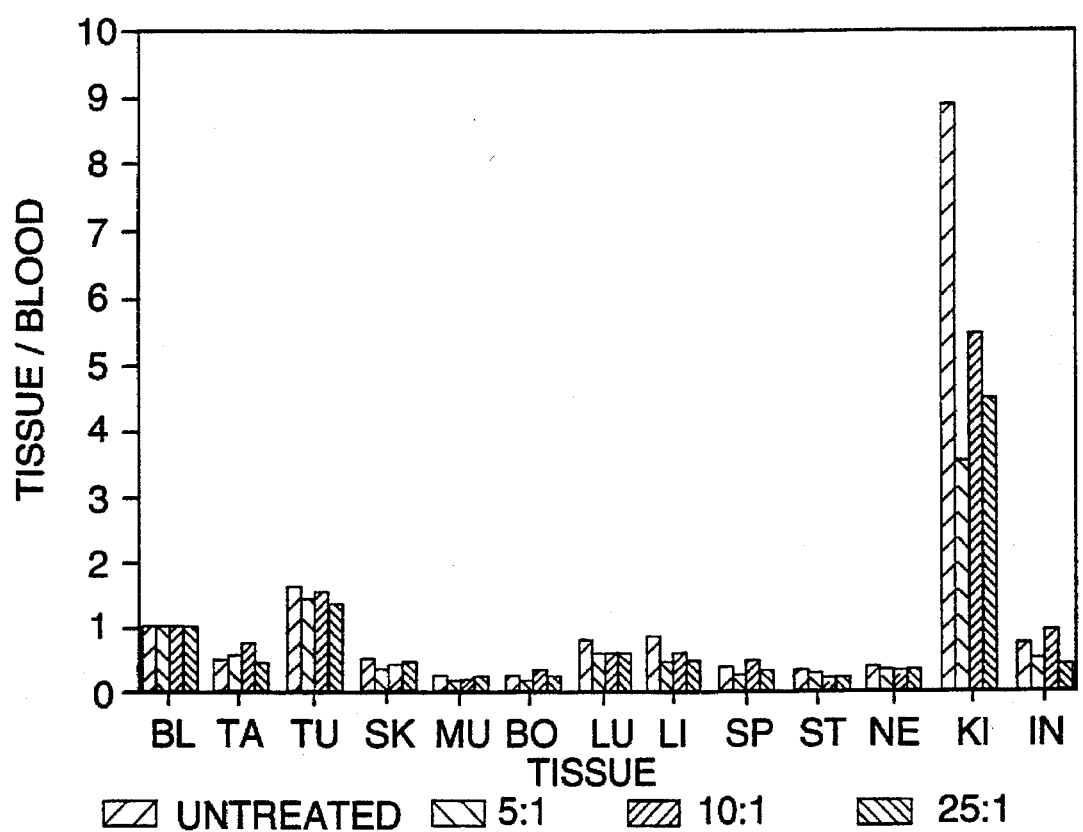
FIG. 5 is another whole animal biodistribution and tumor localization profile of succinylated (at three molar ratios) monoclonal antibody. The procedure followed was the same as in FIG. 4, except that the mice were sacrificed at 6 hours post administration, before all of the radiolabel was excreted from the kidneys. The figure legends are: BL=blood; TA=tail; TU=tumor; SK=skin; MU=muscle; BO=bone; LU=lung; LI=liver; SP=spleen; ST=stomach; NE=neck; KI=kidney; and IN=intestine.

At earlier than 20-hour time points of examination, there are dramatic differences noted in the kidney accumulation of radiolabeled antibody fragments, with charge-modified (5:1 to 25:1 offering molar ratios) antibody fragments having lower kidney accumulation (see FIG. 5). Therefore, these data indicate that charge modification of whole monoclonal antibodies or monoclonal antibody fragments can increase tumor uptake by increasing serum half-life through reduced renal accumulation and excretion.

Accordingly, the altered excretion rate of a charge-modified antibody or antibody fragment is responsible for higher tumor accumulations. However, as illustrated in Example 3, the increase in affinity after succinylation may also be responsible for an increase in the percent dose/gram in tumor.

EXAMPLE 6

The Effect of Succinylization on the Immunogenicity of Antibody

The effect on immunogenicity of charge-modified antibodies was tested by immunizing guinea pigs with heterologous murine antibodies (either charge-modified or unmodified). Charge modification of NR-CO-04 resulted in lower levels of antiglobulin produced by the host guinea pig against the murine antibodies. This result was produced both in immunization protocols employing one injection as well as protocols employing multiple injections. These results indicate that one can reduce immunogenicity and improve the probability that a patient can receive multiple injections of charge-modified murine antibodies, antibody fragments, or other targeting proteins.

EXAMPLE 7

Charge Modification—Succinylation Reaction

Succinic anhydride is dissolved in anhydrous DMSO (or other dry organic solvent) at a concentration of 40 mg per 200 μl (final vol. 231 μl, 1.73M). A 25 μl aliquot is diluted up to 2.5 ml in anhydrous DMSO ($1.73 \times 10^{-2}$M) as the working solution. The working solution is added with rapid stirring to the protein solution, 3–5 mg/ml in carbonate/ bicarbonate buffer, pH 8.5–9.0, at the desired molar ratio (e.g., 1:5, 1:10, 1:25 antibody or antibody fragment to succinic anhydride). The reaction is conducted at room temperature for 15–30 min. Succinic acid (which results from the rapid hydrolysis of anhydride) is removed by ultrafiltration (e.g., Amicon or Centricon) or by gel filtration using Sephadex G-25. The PI's of both modified and unmodified proteins are determined by isoelectric focusing.

EXAMPLE 8

Charge Modification Using Glucose-6-Phosphate

A targeting protein is charge-modified using glucose-6-phosphate as the anion-forming reagent. The reagent is attached to the protein in a non-enzymatic glycosylation reaction which may be depicted by the following reaction scheme:

wherein the targeting protein is represented as "P" and the glucose-6-phosphate reacts with a primary amine on the protein. The reaction is conducted in the presence of NaBH$_3$CN to drive the reaction toward the desired product, rather than favoring possible side reactions (not shown). The +1 charge on the lysine residue is changed to a –2 charge.

It is apparent from the foregoing examples that many conjugates of radionuclides, drugs and toxins as well as targeting proteins, have poor tumor delivery characteristics, including short serum half-lives. Charge modification to impart negative charges to the conjugates, or preselection of native fragments with appropriate isoelectric points, can increase their serum half-life and bioavailability to the tumor and thus improve their efficacy.

From the foregoing, it will be appreciated that, although specific embodiments of the invention have been described herein for purposes of illustrations, various modifications may be made without departing from the spirit and scope of the invention.

What is claimed is:

1. A conjugate comprising a monoclonal antibody or fragment thereof and a charge-modified polypeptide toxin, wherein the charge-modified toxin contains at least one non-native anionic group formed by reaction of at least one native amino group of unmodified toxin with an anion-forming agent.

2. The conjugate of claim 1 wherein the monoclonal antibody or fragment thereof also is charge-modified by reaction with an anion-forming agent which modifies a group on the monoclonal antibody or fragment thereof to an anionic group.

3. The conjugate of claim 1 or 2 wherein the anion-forming agent is of the formula:

$$X—G—Y$$

wherein X is a functional group reactive with primary amines on lysine residues or a precursor thereof; G represents an optional organic spacer; and Y is a negatively charged ion or a precursor thereof.

4. The conjugate of claim 3 wherein the anion-forming agent comprises an anhydride and/or at least one carboxylic acid group.

5. The conjugate of claim 1 or 2 wherein the polypeptide toxin is Pseudomonas exotoxin or a fragment thereof.

6. The conjugate of claim 1 containing at lease one non-native anionic group formed by reaction of at least one native lysine group of an unmodified polypeptide toxin with an anion-forming agent.

7. The polypeptide toxin of claim 6 wherein said toxin is Pseudomonas exotoxin or a fragment thereof.

8. A conjugate comprising the polypeptide toxin of claim 6 or 7 and a monoclonal antibody or fragment thereof.

9. The conjugate of claim 6, wherein less than about 10% of the native lysine groups on the unmodified conjugate are reacted with the anion-forming agent.

10. The conjugate of claim 1 wherein the charge-modified polypeptide toxin contains sufficient non-native anionic groups to effect an acidic shift of at least ⅟₁₀ of a pH unit in the isoelectric point compared to the unmodified toxin and to increase the serum half-life of the conjugate by at least about 10% compared to a conjugate of the monoclonal antibody or fragment thereof and the unmodified toxin.

11. The conjugate of claim 10 wherein the charge-modified polypeptide toxin contains sufficient non-native anionic groups to effect a shift of about 1 pH unit in the isoelectric point compared to the unmodified toxin.

* * * * *